United States Patent [19]
Sato

[11] Patent Number: 5,496,506
[45] Date of Patent: Mar. 5, 1996

[54] PROCESS FOR REMOVING FINE PARTICLES

[75] Inventor: Junichi Sato, Tokyo, Japan

[73] Assignee: Sony Corporation, Tokyo, Japan

[21] Appl. No.: 121,366

[22] Filed: Sep. 15, 1993

[30] Foreign Application Priority Data

Sep. 21, 1992 [JP] Japan .................................. 4-250306

[51] Int. Cl.$^6$ ................................................ H01L 21/304
[52] U.S. Cl. .......................... 264/400; 134/902; 264/233; 264/482; 427/535; 437/946
[58] Field of Search ........................ 134/902; 437/946; 427/534, 96, 485, 486, 536, 535; 264/81–83, 85, 233, 22

[56] References Cited

FOREIGN PATENT DOCUMENTS

| | | | |
|---|---|---|---|
| 516480 | 12/1992 | European Pat. Off. ............... | 437/946 |
| 52-75183 | 6/1977 | Japan .................................... | 437/946 |
| 56-121632 | 9/1981 | Japan .................................... | 437/946 |
| 57-76846 | 5/1982 | Japan .................................... | 437/946 |
| 57-102229 | 6/1982 | Japan .................................... | 437/946 |
| 58-42238 | 3/1983 | Japan .................................... | 437/946 |
| 63-90138 | 4/1988 | Japan .................................... | 134/902 |
| 63-276229 | 11/1988 | Japan .................................... | 134/902 |
| 3-127830 | 5/1991 | Japan .................................... | 134/902 |
| 4-260326 | 9/1992 | Japan .................................... | 134/902 |
| 5-47732 | 2/1993 | Japan .................................... | 134/902 |
| 5-94977 | 4/1993 | Japan .................................... | 134/902 |

*Primary Examiner*—Mathieu D. Vargot
*Attorney, Agent, or Firm*—Hill, Steadman & Simpson

[57] ABSTRACT

A process for detecting fine particles includes the steps of forming a sublimable thin film on an essential surface of a wafer on which fine particles are present, irradiating laser beam at the surface of the wafer, receiving a reflected beam from the surface which is scattered by the presence of the fine particles, and detecting the particles from the received scattered beam. The process may further include the step of accomplishing an etchback against the sublimable film to partially retain the sublimable film adjacent the surface of the fine particles. The film can be prepared from one or a mixture of gases including free sulfur generatable gas under discharge-dissociation conditions. Sulfur compounds or polythiazyl are preferable. Alternatively, the film can be made of a condensed film of organic solvent vapor. The sublimable film is sublimed by heating after the step of detecting the fine particles.

16 Claims, 7 Drawing Sheets

PROCESS FOR REMOVING FINE PARTICLES

BACKGROUND OF THE INVENTION

1. Field of the Invention

The present invention relates generally to a process for detecting fine particles present on a surface of a semiconductor wafer. Specifically, the present invention relates to a process for optically detecting fine particles present on the surface of the semiconductor wafer. The present invention also relates to a process for removing such fine particles that were detected from the wafer surface.

2. Description of the Background Art

Recently, a remarkable advance has been made in the technology of semiconductor devices to provide a semiconductor integrate circuits with finer and multi-laying structures. As a fine processing of such circuits, various techniques, such as lithography and dry etching, have been well known. Cleaning technique to detect and remove fine particles which may be present on a surface of the circuit becomes more and more important according to the progress of the fine processing. In the near future, detecting accuracy of fine particles will be increased to the level such that 0.2 to 0.1 μm or less of mean diameter thereof can be detected, though 0.3 μm thereof is enough to obtain the cleaned wafer now.

Conventionally, particles having fine mean diameter present on the semiconductor wafer have been detected by laser beam irradiation. Referring to FIG. 7(A), a wafer 1, on which fine particles 2 may be present, is irradiated with laser beam 3 from one direction. Then, the laser beam 3 is reflected from the wafer surface 1. If fine particles 2 are present on the wafer surface 1, reflection of the laser beam 3 is scattered at the areas where particles 2 are present because of curved surfaces of particles. Sizes and distribution of particles can be detected from the scattering rate of the reflected beam.

However, because detecting sensitivity of the conventional process depends on the scattering rate of the laser beam, particles having very small diameters cannot be detected. For example, as shown in FIG. 7 (B), the laser beam 3 which irradiates such fine particles 2' are not specifically scattered. When an upper layer 4 is laid on the wafer surface 1, as shown in FIG. 7(C), the particle 2' is coated with the layer which causes an apparent diameter thereof to be enlarged. Therefore, during an integrating process of the wafer and layers to an integrated circuit, particles 2' which remains on the wafer surface 1 and which are not detected preliminarily, become accentuated. Particles not detected before the layer 4 formation are now found. These particles, which are called microdust, do not influence the article performance but deteriorate an outer appearance thereof.

Alternatively, deposition of an upper film on the wafer by means of chemical vapor deposition (CVD) can be done to make particles conspicuous. However, the upper film must be removed by mechanical techniques, such as etching, which tends to cause the wafer surface to be damaged. In addition, the process of forming the upper layer is a kind of a destructive test, therefore, a process for non-destructive detection has been required.

Fine particles on the wafer once detected must be removed before laying the upper layer thereon. Japanese Patent First Publication No. 3-152928, of which an inventor is the same as that of the present invention, discloses a process for removing fine particles which were detected. A wafer is chilled to freezing temperatures to freeze the wafer with fine particles present thereon. Then, the frozen particles are removed by applying physical force, such as jetting pressurized gas, onto the wafer surface. However, freezing of the wafer is done by taking advantage of moisture remains in a chilling system in which the wafer is placed. Therefore, when frozen moisture is evaporated after removing particles, contaminants which got mixed with the moisture still remaining on the wafer surface. Also, water marks, which marks formed by moisture evaporation, are frequently remain thereon.

SUMMARY OF THE INVENTION

It is therefore a principal object of the present invention to provide a process for detecting and removing fine particles present on a wafer surface using non-destructive techniques.

It is an additional object of the present invention to provide a process for detecting fine particles having very small diameters that are present on a wafer.

It is a further object of the present invention to provide a process for removing such detected fine particles without creating water marks and damages.

It is another object of the present invention to provide a process for accurately detecting and removing fine particles present on a wafer surface while allowing the outer appearance thereof to be improved.

In order to accomplish the aforementioned and other objects, the present invention comprises the steps of forming a sublimable thin film on an essential surface of a wafer on which fine particles are present, irradiating a laser beam onto the surface of the wafer, receiving a reflected beam from the surface which is scattered by the presence of the fine particles, and detecting the particles by the received scattered beam.

The process can further comprise the step of accomplishing an etchback against an essential surface of the sublimable film, to partially retain the sublimable film adjacent the surface of the fine particles.

The sublimable film can be prepared from one gas or a mixture of gases including free sulfur generatable gases under discharge-dissociation conditions. The free sulfur generatable gas can be selected from the groups consisting of $S_2F_2$, $SF_2$, $SF_4$, $S_2F_{10}$, $S_3Cl_2$, $S_2Cl_2$, $SCl_2$, $S_3Br_2$, $S_2Br_2$, and $SBr_2$. Nitrogen gas may be included. Sulfur or polythiazyl compounds are preferable.

Alternatively, the sublimable film can be made of a condensed film of organic solvent vapor.

The process of the present invention further comprises the step of subliming the sublimable film by heating the wafer on which the sublimable film is formed to remove the film from the wafer surface after the step of detecting the fine particles.

Supplying jetting flow of highly pressurized inert gas to the wafer surface may be done to remove fine particles with the sublimable film from the wafer surface.

BRIEF DESCRIPTION OF THE DRAWINGS

The present invention will be understood more fully from the detailed description given herebelow and from the accompanying drawings of the preferred embodiments of the invention. However, the drawings are not intended to imply limitation of the invention to a specific embodiment, but are for explanation and understanding only.

In the drawings.

DESCRIPTION OF THE PREFERRED EMBODIMENT

EMBODIMENT 1

Figure 1A:
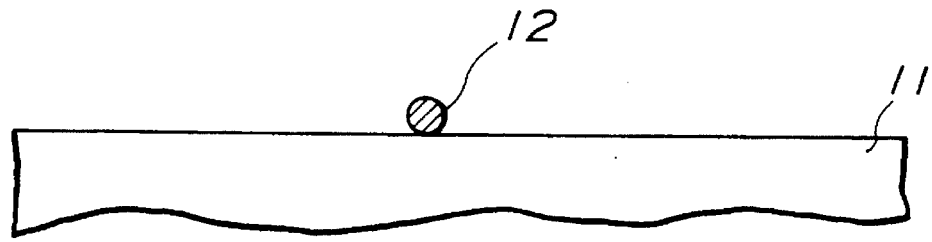
FIGS. 1(A) to (C) are cross sectional views illustrating a process of a first embodiment according to the present invention.
Figure 1B:
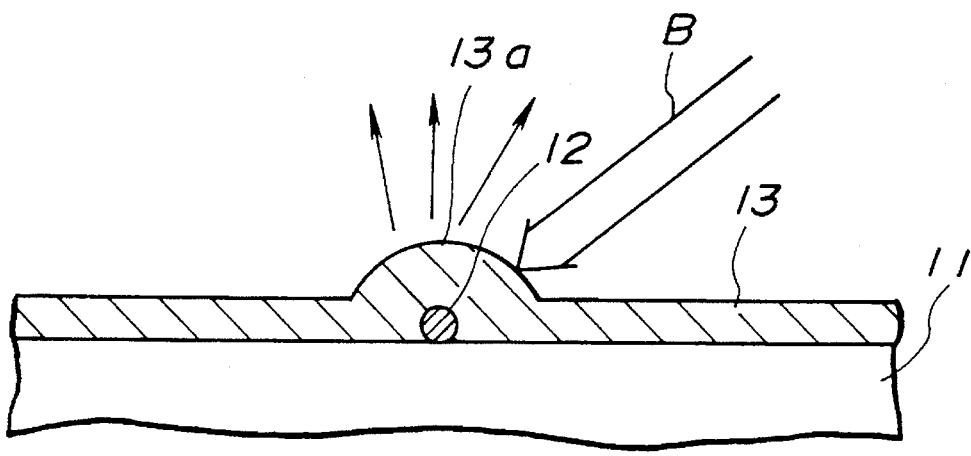
Figure 1C:
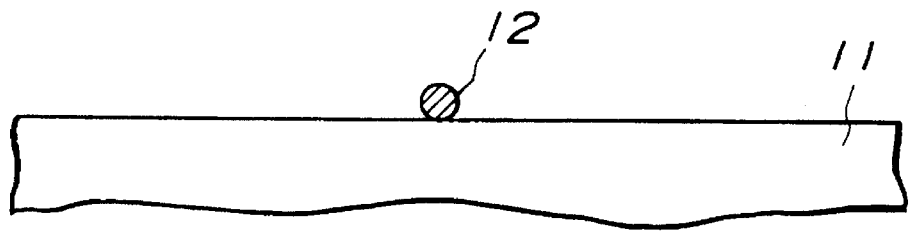
Figure 2:
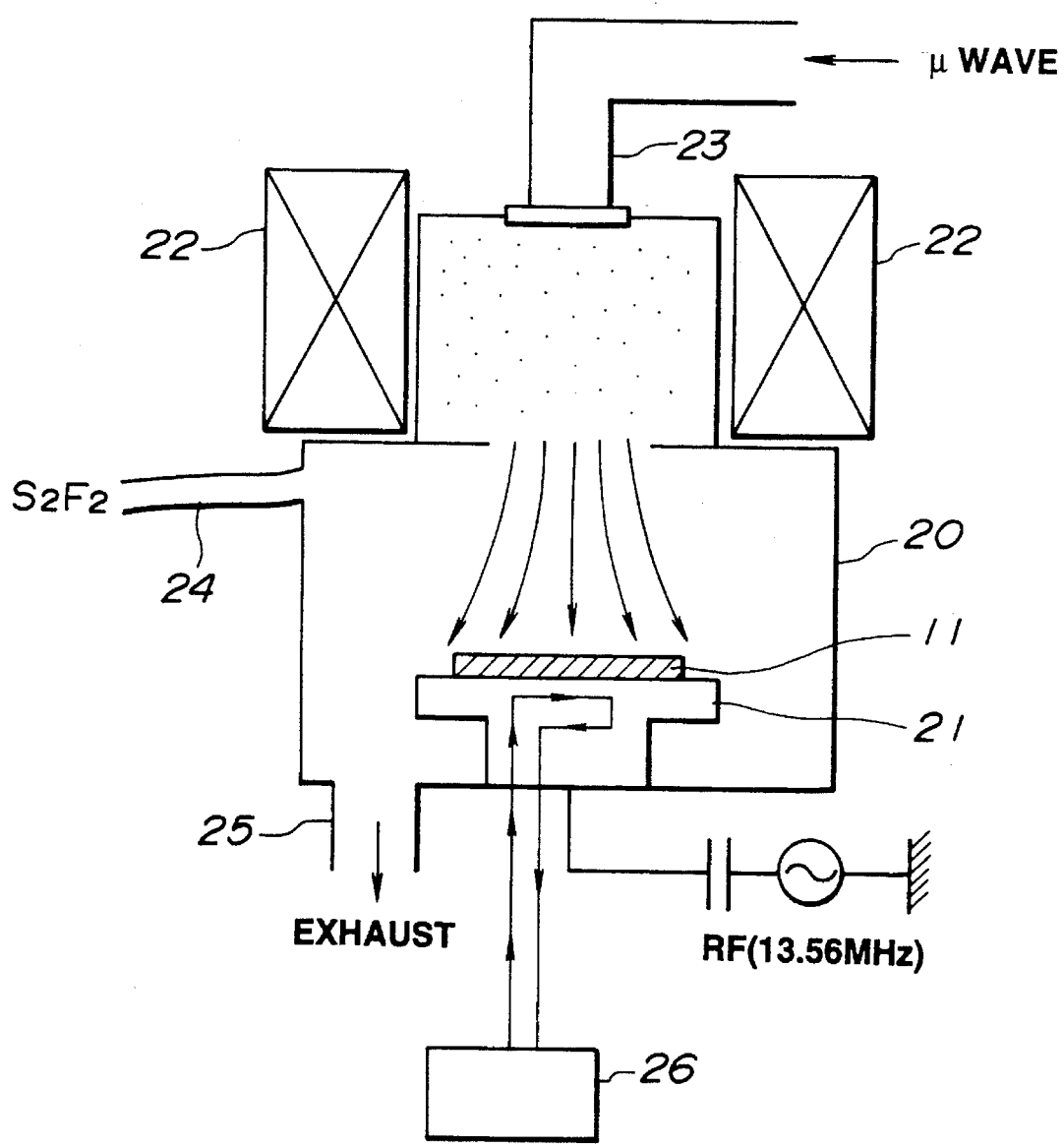
FIG. 2 is a schematic view of a magnetic microwave plasma CVD system utilized during the process of the first embodiment.

Referring now to FIGS. 1(A) to (C), a wafer 11 made of semiconductor material, such as silicon, on which surface particles 12 having very small diameters may be present, is subjected to chemical vapor deposition (CVD) to deposit a sulfur film 13 as a sublimable film on the wafer surface. CVD is done under following conditions utilizing a magnetic microwave plasma CVD system as illustrated in FIG. 2.

| CVD Conditions for Sulfur Film | |
|---|---|
| Flow Rate of Gas $S_2F_2$ | 5 SCCM |
| Pressure | 1.3 Pa |
| Microwave Output | 850 W |
| RF Bias Voltage | 0 W |
| Wafer Temperature | −70° C. |

The magnetic microwave plasma CVD system includes a chamber 20, a wafer stage 21 to place the wafer 11 thereon, a coil 22 and a microwave path 23 respectively installed in an upper portion of the chamber 20. A supply conduit 24 is connected to the upper side wall of the chamber 20 to provide fluidly communication for $S_2F_2$ gas, and an exhaust conduit 25 is connected to the bottom surface of the chamber 20 to exhaust the gas. RF bias voltage is applied to the wafer stage 21. A chiller 26 is connected to the wafer stage 21 to control temperatures thereof for providing substantial chilling to the wafer 11. Thickness of the sulfur film may be determined to 200 nm.

Referring now again to FIG. 1(B), the sulfur film 13 deposited by CVD using the aforementioned CVD system has lifted portions 13a partially lifted from the surface where fine particles 12 are present because the sulfur film 13 is substantially thinned. Each lifted portion 13a has enlarged shape of that of the particle 12 present therebelow.

The wafer 11 on which the sulfur film 13 is laid is introduced into a fine particles detecting system to irradiate laser beam B from one direction toward the surface of the sulfur film 13. Laser beam B is reflected from the film surface and is scattered at the areas where the lifted portions 13a are present. This allows presence and distribution of fine particles 12 on the wafer surface to be detected.

After detecting particles, the wafer 11 with the sulfur film 13 is subjected to heating on a heating stage (not shown in FIG. 2) to sublime the sulfur film from the wafer surface, as shown in FIG. 1(C). For sublimation, the wafer is heated to the temperature of sulfur sublimable. It is prefer to determine the heating temperature at not less than 100° C.

EMBODIMENT 2

A film of polythiazyl compound $((SN)_x)$ is deposited on a wafer surface by CVD under following conditions.

| CVD Conditions for $(SN)_x$ Film | |
|---|---|
| Flow Rate of Gas | |
| $S_2F_2$ | 5 SCCM |
| $N_2$ | 5 SCCM |
| Pressure | 1.3 Pa |
| Microwave Output | 850 W |
| RF Bias Voltage | 0 W |
| Wafer Temperature | −70° C. |
| Thickness of the Film | 200 nm |

Fine particles present on the wafer surface can be accentuated by depositing the $(SN)_x$ film. The wafer on which the $(SN)_x$ film is laid is introduced into the fine particles detecting system to irradiate laser beam B similar to the process of the embodiment 1. Presence and distribution of fine particles on the wafer surface are easily detected.

After detecting particles, the wafer with the $(SN)_x$ film is subjected to heating to sublime the film from the wafer surface. For sublimation, the wafer is heated to the temperature of $(SN)_x$ sublimable. It is prefer to determine the heating temperature at not less than 100° C.

EMBODIMENT 3

Figure 3A:
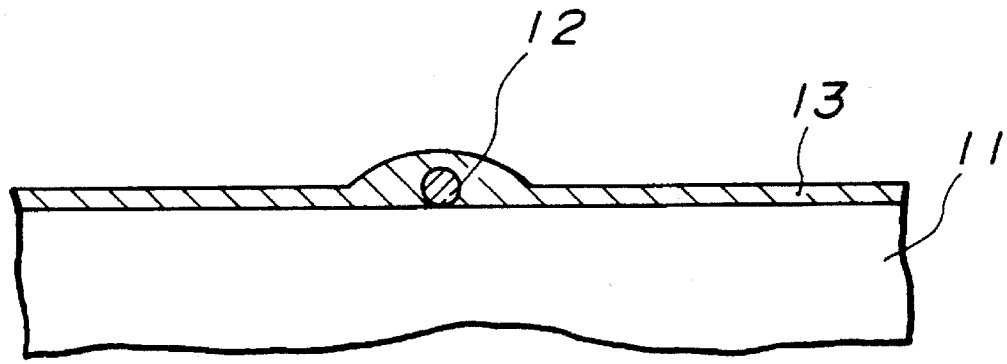
FIGS. 3(A) to (C) are cross sectional views illustrating a process of a third embodiment according to the present invention.
Figure 3B:
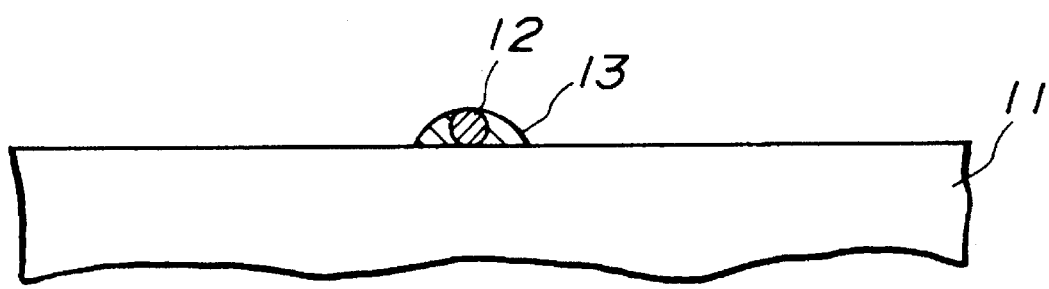
Figure 3C:
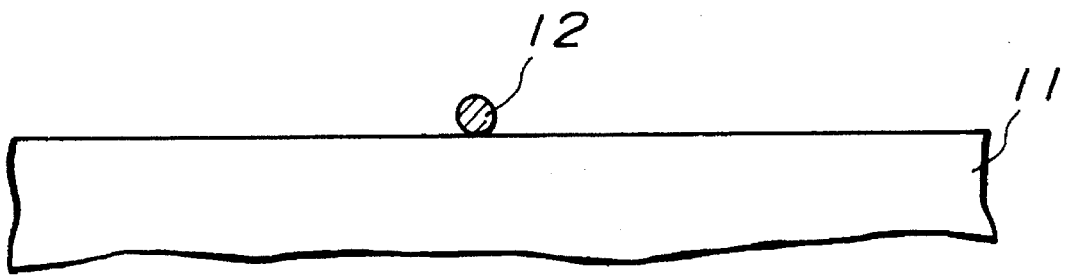

Referring now to FIGS. 3(A) to (C), a sulfur film is deposited on a wafer surface by CVD as described above. Thickness of the film may be determined to 200 nm. Here, in the figures, same numeral as FIGS. 1(A) to (C) are given to the same member as illustrated therein.

The sulfur film is thoroughly subjected to etchback using a magnetic microwave plasma etcher. Conditions of etchback are followed.

| Etchback Conditions | |
|---|---|
| Flow Rate of Gas $SF_6$ | 10 SCCM |
| Pressure | 1.3 Pa |
| Microwave Output | 850 W |
| RF Bias Voltage | 5 W |
| Wafer Temperature | −70° C. |

The sulfur film 13 except adjacent fine particles 12 can be removed after applying etchback, as illustrated in FIG. 3(B). The residue of the sulfur film 13 forms a sulfur coating of the particle 12. This permits an apparent diameter of the fine particles to be sufficiently enlarged. Therefore, the coating can be easily and surely detected by the fine particles detecting system. Thus, presence and distribution of the fine particles can be detected.

After detecting particles, the wafer with the sulfur coatings including particles is subjected to heating to sublime the sulfur coating from the wafer surface. For sublimation of sulfur, the wafer is heated to the temperature for sublimation of the sulfur. The temperature may be prefer to determine at not less than 100° C(refer to FIG. 3(C)).

EMBODIMENT 4

A film of polythiazyl compound $((SN)_x)$ is deposited on a wafer surface by CVD under following conditions. Thickness of the film may be determined to 200 nm.

CVD Conditions for $(SN)_x$ Film

| Flow Rate of Gas | |
|---|---|
| $S_2F_2$ | 5 SCCM |
| $N_2$ | 5 SCCM |
| Pressure | 1.3 Pa |
| Microwave Output | 850 W |
| RF Bias Voltage | 0 W |
| Wafer Temperature | −70° C. |

The polythiazyl compound film is then thoroughly subjected to etchback similarly to the process of the aforementioned embodiment 3. Conditions of etchback are followed.

Etchback Conditions

| Flow Rate of Gas $SF_6$ | 10 SCCM |
|---|---|
| Pressure | 1.3 Pa |
| Microwave Output | 850 W |
| RF Bias Voltage | 5 W |
| Wafer Temperature | −70° C. |

Presence and distribution of fine particles can also be easily and surely detected by the fine particles detecting system similarly to the embodiment 3.

Here, in embodiments 3 and 4, the etching condition is determined to sufficiently minimize ion energy because the wafer surface tends to be damaged thereby. To surely protect the wafer surface from etching, it is also prefer to terminate etching up to 90% thereof. Even though 90% under-etching is done, the film on the wafer surface can be substantially removed. Then, presence and distribution of fine particles can be detected.

After detecting particles, the wafer with the $(SN)_x$ film is subjected to heating to sublime the film from the wafer surface. For sublimation, the wafer is heated to the temperature of $(SN)_x$ sublimation. It is prefer to determine the heating temperature at not less than 100° C.

EMBODIMENT 5

Figure 4:
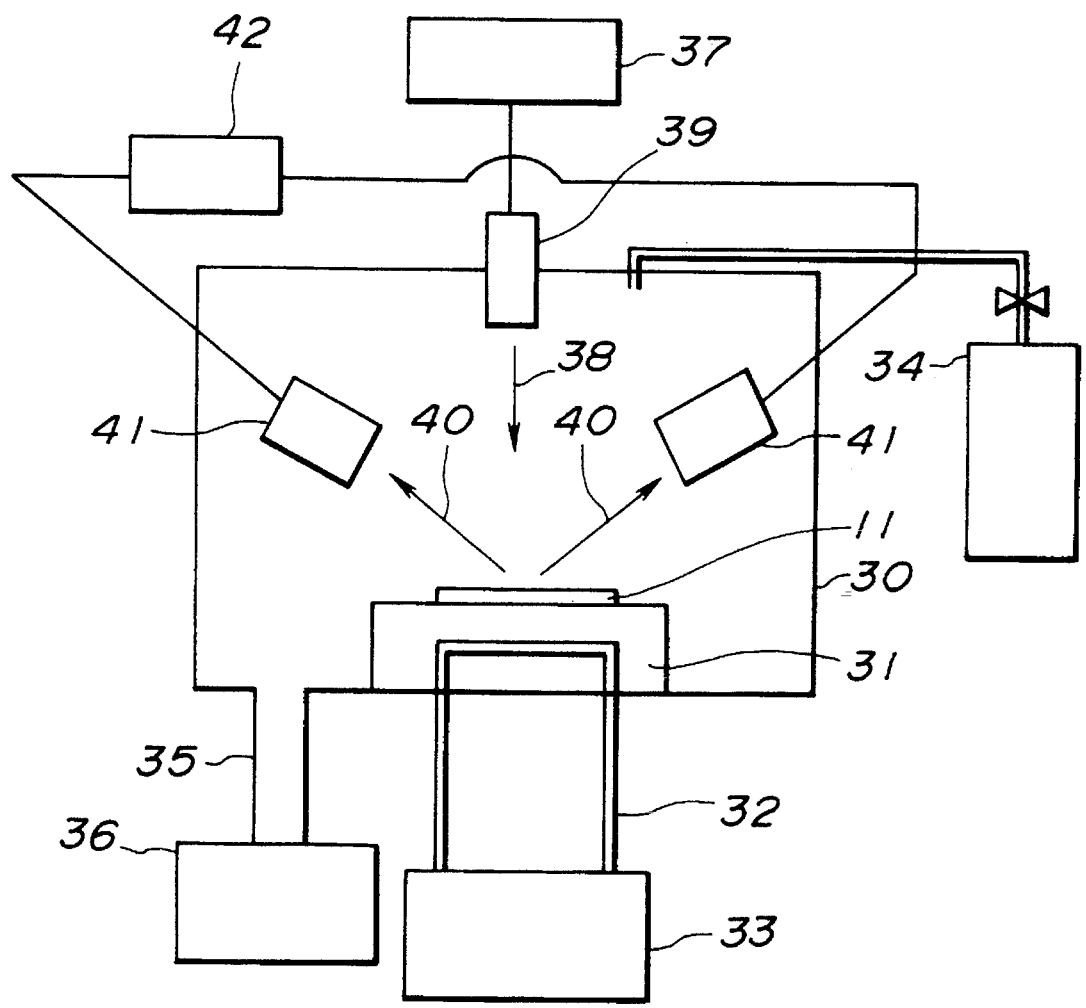
FIG. 4 is a schematic view of a fine particles detecting system utilized during a process of a fifth embodiment according to the present invention.

A wafer is placed in a fine particles detecting system, as illustrated in FIG. 4, then pores of condensed organic solvent vapor, in which particles are nucleated, are formed.

Referring to FIG. 4, a detecting room 30 is installed in the fine particles detecting system. A wafer susceptor 31 is installed on the bottom surface of the detecting room 30 to place a wafer 11 thereon. Refrigerant is supplied to the wafer susceptor 31 from a chiller 33 via a supply conduit 32 to circulate therethrough. The wafer can be chilled to the temperature of −100° C. by the chiller 33. Gas supply means 34 is connected to the detecting room 30 to supply organic solvent, which is vaporized in the gas supply means 34, toward the detecting room 30. An exhaust conduit 35 is also connected to the detecting room 30 to exhaust atmosphere therein to the level of not more than $10^{-5}$ Pa.

When detecting fine particles on the wafer surface, the wafer 11 is irradiated with laser beam 38 generated from a laser beam source 37 via an irradiation system 39. Scattered beam 40 reflected from the wafer surface 11 is monitored by detecting means 41, then converted into informations of particles presence and distribution by a signal processing system 42.

Figure 5A:
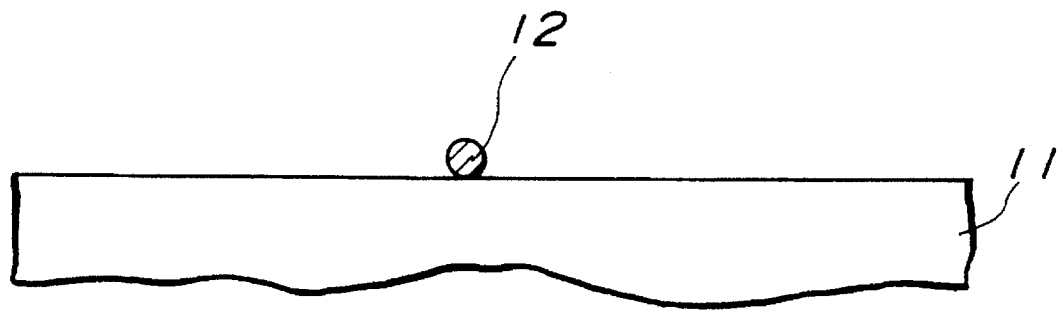
FIGS. 5(A) to (C) are cross sectional views illustrating the process of the fifth embodiment.
Figure 5B:
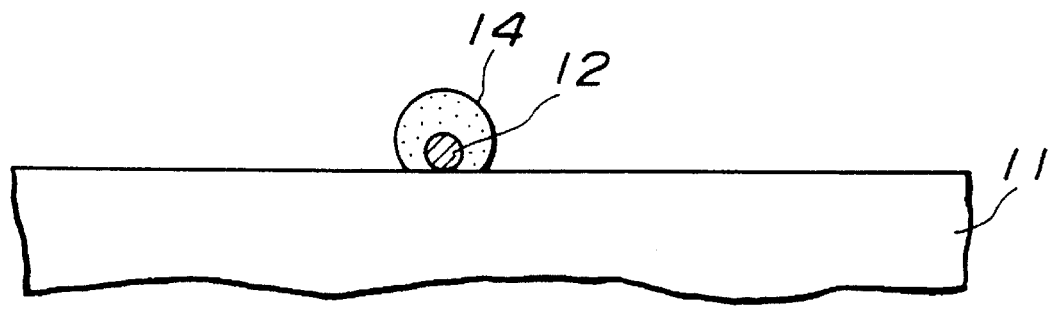
Figure 5C:
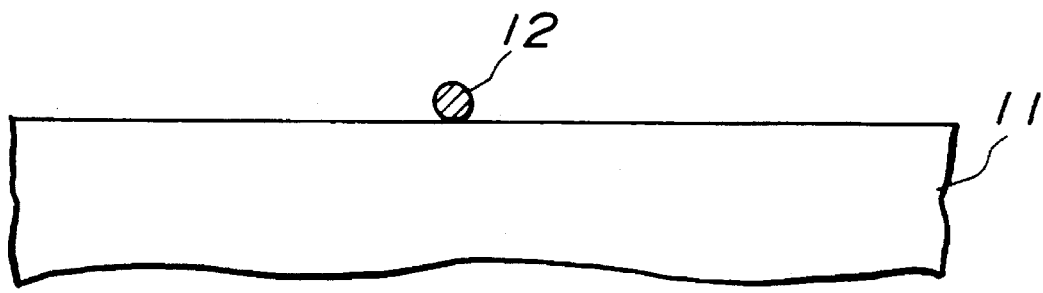

Referring now to FIG. 4 and FIGS. 5(A) to (C) (same numerals are given to the same members as shown in FIGS. 1(A) to (C)), the wafer 11 on which fine particles 12 may be present is placed on the wafer susceptor 31 in the detecting room 30 of the fine particles detecting system of FIG. 4. Vapor of ortho-xylene (having a boiling point of 144° C.) is supplied as the organic solvent toward the wafer surface. Then, the wafer 11 is chilled by operating the chiller 33 to form a condensed pore 14 of ortho-xylene at the surrounding of the particle 12 as a condensation nucleus, as illustrated in FIG. 5(B). Presence of the particle 12 is accentuated by the surrounding ortho-xylene pore 14. Therefore, presence and distribution of fine particles 12 can be surely and easily detected.

After detecting particles, the wafer 11 is subjected to heating to sublime the ortho-xylene pores from the wafer surface. For sublimation, the wafer is heated to the temperature of ortho-xylene sublimable. It is prefer to determine the heating temperature at not less than 100° C. Thus, the pores of ortho-xylene can be easily removed (refer to FIG. 5(C)).

In this embodiment, condensation of organic solvent vapor can be selectively occur at only the surroundings of the particles because the particles work as condensation nucleus. Therefore, detection of fine particles becomes more easily.

EMBODIMENT 6

Vapor of di-butyl-phthalate (having a boiling point of 339° C.) is supplied as the organic solvent to the surface of the wafer 11 placed in the detecting room 30. The wafer 11 is then chilled to −50° C. by operation of the chiller 33 to form pores of condensed di-butyl-phthalate at the surrounding of each particle. Thereafter, similarly to the process of the aforementioned embodiment 5, presence and distribution of fine particles are detected.

After detecting particles, the wafer 11 is subjected to heating to sublime the di-butyl-phthalate pores from the wafer surface. For sublimation, the wafer is heated to the temperature of di-butyl-phthalate sublimable. It is prefer to determine the heating temperature at not less than 200° C. Thus, the condensed pores can be easily removed from the wafer surface.

EMBODIMENT 7

Figure 6A:
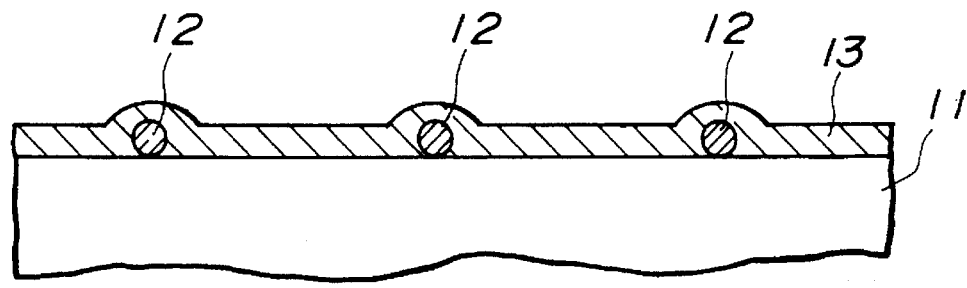
FIGS. 6(A) to (C) are cross sectional views illustrating a process of a seventh embodiment according to the present invention.
Figure 6B:
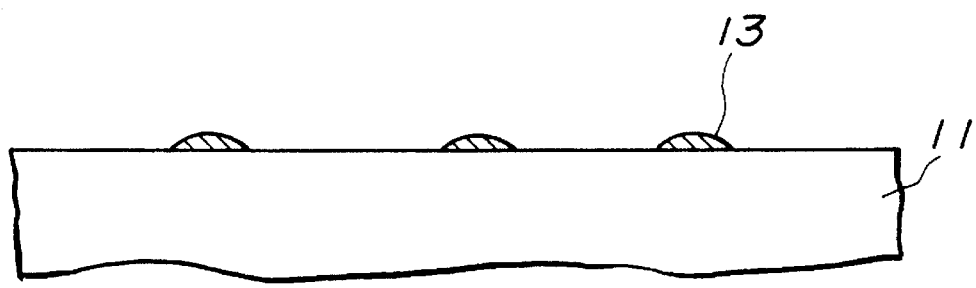
Figure 6C:
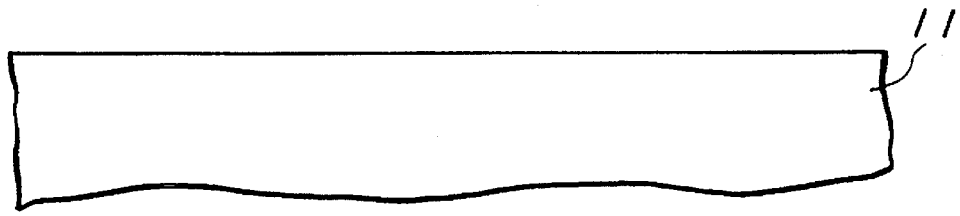
Figure 7A:
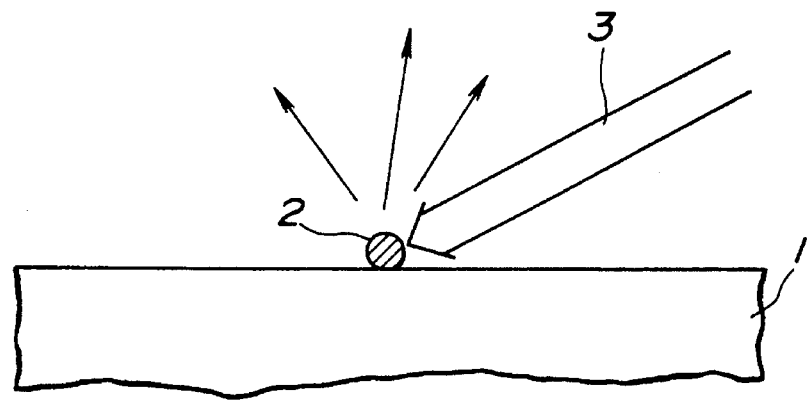
FIGS. 7(A) to (C) are cross sectional views showing detections by the prior art.
Figure 7B:
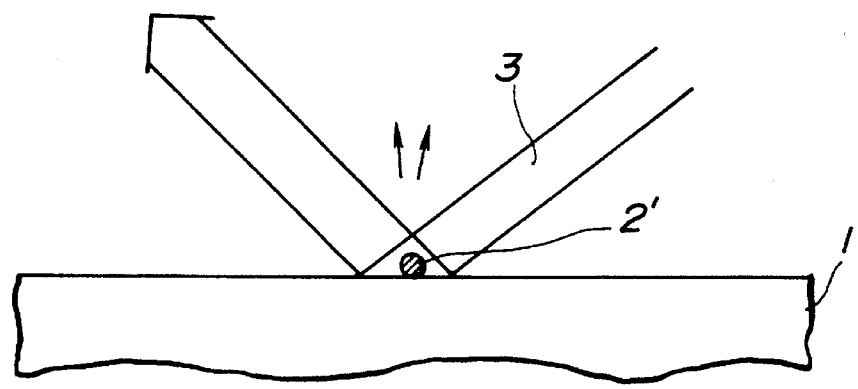
Figure 7C:
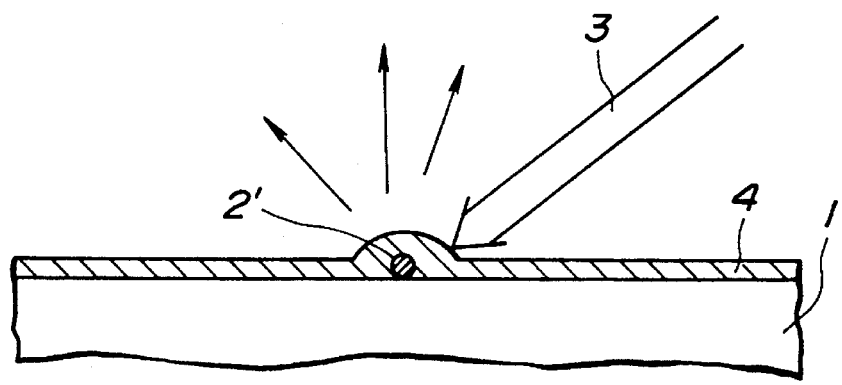

Referring now to FIGS. 6(A) to (C) in which same numerals are given to the same members as shown in FIGS. 1(A) to (C).

A wafer is introduced into the magnetic microwave plasma CVD system, then vacuumed to $10^{-7}$ Pa in order to prevent the influence of residual moisture. Then, a sulfur film 13 is deposited on the wafer surface to coat fine particles 12 present thereon, as shown in FIG. 6(A). The thickness of the sulfur film is preferably determined to 100 nm. Conditions of CVD are followed.

| CVD Conditions for Sulfur Film | |
| --- | --- |
| Flow Rate of Gas $S_2F_2$ | 5 SCCM |
| Pressure | 1.3 Pa |
| Microwave Output | 850 W |
| RF Bias Voltage | 0 W |
| Wafer Temperature | −70° C. |

Then, the wafer 11 is transferred to a washing room connected to the CVD system via a gate valve (both are not shown in the figures). Nitrogen gas is jetted to the wafer surface via a jet blow system (not shown in the figures). The particles 12 is directly removed thereby from the wafer surface with the sulfur film 13. Especially, the surface of the sulfur film 13 is lifted at the area where the particle 12 is present, therefore, the particle 12 is easily removed by the jetted gas. When the sulfur film 13 is retained on the wafer surface 11 after jetting, as illustrated in FIG. 6(B), the remaining film can be easily removed by heating the wafer 11 to the temperature of sulfur sublimation, preferably at not less than 100° C. (refer to FIG. 6(C)).

EMBODIMENT 8

A wafer is introduced into the magnetic microwave plasma CVD system at a vacuum of $10^{-7}$ Pa. Then, a polythiazyl compound film is deposited on the wafer surface to coat fine particles present thereon. The thickness of the polythiazyl compound film is preferably determined to 100 nm. Conditions of CVD are followed.

| CVD Conditions for $(SN)_x$ Film | |
| --- | --- |
| Flow Rate of Gas | |
| $S_2F_2$ | 5 SCCM |
| $N_2$ | 5 SCCM |
| Pressure | 1.3 Pa |
| Microwave Output | 850 W |
| RF Bias Voltage | 0 W |
| Wafer Temperature | −70° C. |

Then, fine particles are removed from the wafer surface with the polythiazyl film by the process similar to the aforementioned embodiment 7.

While the present invention has been disclosed in terms of the preferred embodiment in order to facilitate better understanding of the invention, it should be appreciated that the invention can be embodied in various ways without depending from the principle of the invention. Therefore, the invention should be understood to include all possible embodiments and modification to the shown embodiments which can be embodied without departing from the principle of the inventions as set forth in the appended claims.

For example, the sublimable film is not limited to sulfur and polythiazyl compound. One or a mixture of Gases including free sulfur generatable gas under discharge-dissociation conditions may be utilized to form the film. Temperature of the wafer must be regulated at not more than ordinary temperatures when the film is deposited. The free sulfur generatable gas may be selected from the groups consisting of $S_2F_2$, $SF_2$, $SF_4$, $S_2F_{10}$, $S_3Cl_2$, $SCl_2$, $S_3Br_2$, $S_2Br_2$, and $SBr_2$. The organic solvent for condensation is not limited to ortho-xylene and di-butyl-phthalate, but various solvent can be utilized.

What is claimed is:

1. A process for removing fine particles from a wafer surface of a wafer comprising the steps of:

forming a sublimable thin film on the wafer surface which has fine particles thereon, and removing the fine particles with the sublimable film from the wafer surface by supplying a jetting flow of highly pressurized inert gas to said wafer surface.

2. A process as set forth in claim 1, wherein said sublimable film is made of sulfur.

3. A process as set forth in claim 2, wherein said sublimable film is prepared from one or a mixture of gases including free sulfur generatable gas under discharge-dissociation conditions.

4. A process as set forth in claim 3, wherein said free sulfur generatable gas is selected from the group consisting of $S_2F_2$, $SF_2$, $SF_4$, $S_2F_{10}$, $S_3Cl_2$, $S_2Cl_2$, $SCl_2$, $S_3Br_2$, $S_2Br_2$, and $SBr_2$.

5. A process as set forth in claim 1, wherein said sublimable film is made of polythiazyl.

6. A process as set forth in claim 5, wherein said sublimable film is prepared from one or a mixture of gases including free sulfur generatable gas under discharge-dissociation conditions and nitrogen.

7. A process as set forth in claim 6, wherein said free sulfur generatable gas is selected from the group consisting of $S_2F_2$, $SF_2$, $SF_4$, $S_2F_{10}$, $S_3Cl_2$, $S_2Cl_2$, $SCl_2$, $S_3Br_2$, $S_2Br_2$, and $SBr_2$.

8. A process according to claim 1, wherein the step of removing includes heating to facilitate removal of the film.

9. A process according to claim 1, which includes a step of detecting the fine particles after the step of forming the film and before the step of removing the film and particles.

10. A process according to claim 9, wherein the step of removing includes heating to aid the removal of the film.

11. A process for removing fine particles from a wafer surface of a wafer comprising the steps of:

forming a sublimable thin film containing sulfur on the wafer surface which has fine particles thereon, and supplying a jetting flow of highly pressurized inert gas to said wafer surface to remove the fine particles with said sublimable film of sulfur from the wafer surface.

12. A process according to claim 11, wherein said sublimable film is prepared from one or a mixture of gases including free sulfur generatable gas under discharge-dissociation conditions.

13. A process according to claim 12, wherein said free sulfur generatable gas is selected from the group consisting of $S_2F_2$, $SF_2$, $SF_4$, $S_2F_{10}$, $S_3Cl_2$, $S_2Cl_2$, $SCl_2$, $S_3Br_2$, $S_2Br_2$, and $SBr_2$.

14. A process according to claim 11, wherein said sublimable film is made of polythiazyl.

15. A process according to claim 14, wherein said sublimable film is prepared from one or a mixture of gases including free sulfur generatable gas under discharge-dissociation conditions and nitrogen.

16. A process according to claim 15, wherein said free sulfur generatable gas is selected from the group consisting of $S_2F_2$, $SF_2$, $SF_4$, $S_2F_{10}$, $S_3Cl_2$, $S_2Cl_2$, $SCl_2$, $S_3Br_2$, $S_2Br_2$, and $SBr_2$.

* * * * *